United States Patent
Van Slyke et al.

(10) Patent No.: US 9,554,712 B2
(45) Date of Patent: Jan. 31, 2017

(54) SYSTEMS AND METHODS FOR GENERATING AN ARTIFICIAL PHOTOPLETHYSMOGRAPH SIGNAL

(71) Applicant: Covidien LP, Mansfield, MA (US)

(72) Inventors: Braddon M. Van Slyke, Arvada, CO (US); Ronald Kadlec, Longmont, CO (US); Scott McGonigle, Edinburgh (GB); Michael Mestek, Superior, CO (US); Paul Stanley Addison, Edinburgh (GB); James Nicholas Watson, Dunfermline (GB)

(73) Assignee: Covidien LP, Mansfield, MA (US)

( * ) Notice: Subject to any disclaimer, the term of this patent is extended or adjusted under 35 U.S.C. 154(b) by 961 days.

(21) Appl. No.: 13/779,487

(22) Filed: Feb. 27, 2013

(65) Prior Publication Data
US 2014/0244205 A1    Aug. 28, 2014

(51) Int. Cl.
| | |
|---|---|
| *A61B 5/024* | (2006.01) |
| *A61B 5/1455* | (2006.01) |
| *A61B 5/1495* | (2006.01) |
| *A61B 5/00* | (2006.01) |
| *A61B 5/0205* | (2006.01) |

(52) U.S. Cl.
CPC ......... *A61B 5/02416* (2013.01); *A61B 5/1495* (2013.01); *A61B 5/14551* (2013.01); *A61B 5/7278* (2013.01); *A61B 5/0205* (2013.01)

(58) Field of Classification Search
CPC ................................................ A61B 5/02416
See application file for complete search history.

(56) References Cited

U.S. PATENT DOCUMENTS

| | | | |
|---|---|---|---|
| 3,846,704 A | 11/1974 | Bessette | |
| 4,063,551 A | 12/1977 | Sweeney | |
| 4,458,518 A | 7/1984 | Ingle | |
| 4,958,638 A | 9/1990 | Sharpe et al. | |
| 5,188,108 A | 2/1993 | Secker | |

(Continued)

FOREIGN PATENT DOCUMENTS

| | | |
|---|---|---|
| EP | 0072601 A1 | 2/1983 |
| EP | 1344488 A2 | 9/2004 |

(Continued)

OTHER PUBLICATIONS

Stagg and Gennser, "Electronic analysis of foetal breathing movements: A practical application of phase-locked-loop principles," Journal of Med. Eng. and Tech., Sep. 1978, vol. 2, No. 5, pp. 246-249.

(Continued)

*Primary Examiner* — John Breene
*Assistant Examiner* — Jeffrey C Morgan

(57) ABSTRACT

A test unit may generate a pulse signal based on a pulsatile profile and a frequency modulation component of a respiratory profile. A respiration modulated signal may be generated from the pulse signal, an amplitude modulation component, and a baseline modulation component. A patient modulated signal may be generated based on the respiration modulated signal and a patient profile. The artificial PPG signal may be generated based on the patient modulated signal and an artifact profile. The artificial PPG signal may be output to an electronic device.

22 Claims, 10 Drawing Sheets

(56) References Cited

U.S. PATENT DOCUMENTS

| | | | |
|---|---|---|---|
| 5,285,783 A | 2/1994 | Secker | |
| 5,285,784 A | 2/1994 | Secker | |
| 5,368,026 A | 11/1994 | Swedlow et al. | |
| 5,398,682 A | 3/1995 | Lynn | |
| 5,558,096 A | 9/1996 | Palatnik | |
| 5,584,295 A | 12/1996 | Muller et al. | |
| 5,588,425 A | 12/1996 | Sackner et al. | |
| 5,595,176 A | 1/1997 | Yamaura | |
| 5,605,151 A | 2/1997 | Lynn | |
| 5,862,805 A | 1/1999 | Nitzan | |
| 5,865,736 A | 2/1999 | Baker et al. | |
| 5,891,023 A | 4/1999 | Lynn | |
| 6,002,952 A | 12/1999 | Diab et al. | |
| 6,035,223 A | 3/2000 | Baker | |
| 6,081,742 A | 6/2000 | Amano et al. | |
| 6,095,984 A | 8/2000 | Amano et al. | |
| 6,129,675 A | 10/2000 | Jay | |
| 6,135,966 A | 10/2000 | Ko | |
| 6,178,261 B1 | 1/2001 | Williams et al. | |
| 6,223,064 B1 | 4/2001 | Lynn | |
| 6,229,856 B1 | 5/2001 | Diab et al. | |
| 6,238,351 B1 | 5/2001 | Orr et al. | |
| 6,325,761 B1 | 12/2001 | Jay | |
| 6,334,065 B1 | 12/2001 | Al-Ali et al. | |
| 6,342,039 B1 | 1/2002 | Lynn et al. | |
| 6,350,242 B1 | 2/2002 | Doten et al. | |
| 6,405,076 B1 | 6/2002 | Taylor et al. | |
| 6,449,501 B1 | 9/2002 | Reuss | |
| 6,463,311 B1 | 10/2002 | Diab | |
| 6,506,153 B1 | 1/2003 | Littek et al. | |
| 6,561,986 B2 | 5/2003 | Baura et al. | |
| 6,564,077 B2 | 5/2003 | Mortara | |
| 6,606,511 B1 | 8/2003 | Al-Ali et al. | |
| 6,609,016 B1 | 8/2003 | Lynn | |
| 6,684,090 B2 | 1/2004 | Al-Ali et al. | |
| 6,694,178 B1 | 2/2004 | Soula et al. | |
| 6,702,752 B2 | 3/2004 | Dekker | |
| 6,709,402 B2 | 3/2004 | Dekker | |
| 6,748,252 B2 | 6/2004 | Lynn et al. | |
| 6,754,516 B2 | 6/2004 | Mannheimer | |
| 6,760,608 B2 | 7/2004 | Lynn | |
| 6,783,498 B2 | 8/2004 | Sackner et al. | |
| 6,816,741 B2 | 11/2004 | Diab | |
| 6,839,581 B1 | 1/2005 | El Solh et al. | |
| 6,896,661 B2 | 5/2005 | Dekker | |
| 6,905,470 B2 | 6/2005 | Lee et al. | |
| 6,925,324 B2 | 8/2005 | Shusterman | |
| 6,931,269 B2 | 8/2005 | Terry | |
| 6,966,878 B2 | 11/2005 | Schoisswohl et al. | |
| 6,970,792 B1 | 11/2005 | Diab | |
| 6,980,679 B2 | 12/2005 | Jeung et al. | |
| 7,020,507 B2 | 3/2006 | Scharf et al. | |
| 7,035,679 B2 | 4/2006 | Addison et al. | |
| 7,043,293 B1 | 5/2006 | Baura | |
| 7,044,918 B2 | 5/2006 | Diab | |
| 7,070,566 B2 | 7/2006 | Medero et al. | |
| 7,079,888 B2 | 7/2006 | Oung et al. | |
| 7,147,601 B2 | 12/2006 | Marks et al. | |
| 7,177,682 B2 | 2/2007 | Lovett | |
| 7,190,261 B2 | 3/2007 | Al-Ali | |
| 7,215,986 B2 | 5/2007 | Diab et al. | |
| 7,218,966 B2 | 5/2007 | Haefner | |
| 7,254,425 B2 | 8/2007 | Lowery et al. | |
| 7,283,870 B2 | 10/2007 | Kaiser et al. | |
| 7,336,982 B2 | 2/2008 | Yoo | |
| 7,355,512 B1 | 4/2008 | Al-Ali | |
| 7,367,339 B2 | 5/2008 | Hickle | |
| 7,367,949 B2 | 5/2008 | Korhonen et al. | |
| 7,398,115 B2 | 7/2008 | Lynn | |
| 7,403,806 B2 | 7/2008 | Norris | |
| 7,407,486 B2 | 8/2008 | Huiku et al. | |
| 7,415,297 B2 | 8/2008 | Al-Ali et al. | |
| 7,438,683 B2 | 10/2008 | Al-Ali et al. | |
| 7,440,787 B2 | 10/2008 | Diab | |
| 7,470,235 B2 | 12/2008 | Moriya et al. | |
| 7,485,095 B2 | 2/2009 | Shusterman | |
| 7,496,393 B2 | 2/2009 | Diab et al. | |
| 7,499,835 B2 | 3/2009 | Weber et al. | |
| 7,523,011 B2 | 4/2009 | Akiyama et al. | |
| 7,561,912 B2 | 7/2009 | Schatz et al. | |
| 7,610,324 B2 | 10/2009 | Troyansky et al. | |
| 7,690,378 B1 | 4/2010 | Turcott | |
| 7,801,591 B1 | 9/2010 | Shusterman | |
| 7,869,980 B2 | 1/2011 | Casler et al. | |
| 7,887,502 B2 | 2/2011 | Ross et al. | |
| 7,894,868 B2 | 2/2011 | Al-Ali et al. | |
| 7,899,507 B2 | 3/2011 | Al-Ali et al. | |
| 7,976,472 B2 | 7/2011 | Kiani | |
| 7,988,637 B2 | 8/2011 | Diab | |
| 8,019,400 B2 | 9/2011 | Diab et al. | |
| 8,046,040 B2 | 10/2011 | Al-Ali et al. | |
| 8,130,105 B2 | 3/2012 | Al-Ali et al. | |
| 8,203,438 B2 | 6/2012 | Kiani et al. | |
| 8,275,553 B2 | 9/2012 | Amundson et al. | |
| 8,364,223 B2 | 1/2013 | Al-Ali et al. | |
| 8,364,226 B2 | 1/2013 | Diab et al. | |
| 8,755,871 B2 | 6/2014 | Weng et al. | |
| 8,880,576 B2 | 11/2014 | Ochs et al. | |
| 2002/0038078 A1* | 3/2002 | Ito | A61B 5/14551 600/309 |
| 2002/0117173 A1 | 8/2002 | Lynn et al. | |
| 2003/0036685 A1 | 2/2003 | Goodman | |
| 2003/0158466 A1 | 8/2003 | Lynn | |
| 2003/0163054 A1 | 8/2003 | Dekker | |
| 2004/0015091 A1 | 1/2004 | Greenwald et al. | |
| 2004/0225225 A1 | 11/2004 | Naumov et al. | |
| 2005/0004479 A1 | 1/2005 | Townsend et al. | |
| 2005/0022606 A1 | 2/2005 | Partin et al. | |
| 2005/0027205 A1 | 2/2005 | Tarassenko et al. | |
| 2005/0049470 A1 | 3/2005 | Terry | |
| 2005/0070774 A1 | 3/2005 | Addison et al. | |
| 2005/0115561 A1 | 6/2005 | Stahmann et al. | |
| 2005/0222502 A1 | 10/2005 | Cooper | |
| 2005/0222503 A1 | 10/2005 | Dunlop et al. | |
| 2006/0122476 A1 | 6/2006 | Van Slyke | |
| 2006/0192667 A1 | 8/2006 | Al-Ali | |
| 2006/0211930 A1 | 9/2006 | Scharf et al. | |
| 2006/0217614 A1 | 9/2006 | Takala et al. | |
| 2006/0258921 A1 | 11/2006 | Addison et al. | |
| 2007/0004977 A1 | 1/2007 | Norris | |
| 2007/0010723 A1 | 1/2007 | Uetela et al. | |
| 2007/0032639 A1 | 2/2007 | Gottesman et al. | |
| 2007/0073120 A1 | 3/2007 | Li et al. | |
| 2007/0073124 A1 | 3/2007 | Li et al. | |
| 2007/0129636 A1 | 6/2007 | Friedman et al. | |
| 2007/0149890 A1 | 6/2007 | Li et al. | |
| 2007/0213619 A1 | 9/2007 | Linder | |
| 2007/0213621 A1 | 9/2007 | Reisfeld et al. | |
| 2007/0255146 A1 | 11/2007 | Andrews et al. | |
| 2007/0293896 A1 | 12/2007 | Haefner | |
| 2008/0067132 A1 | 3/2008 | Ross et al. | |
| 2008/0077022 A1 | 3/2008 | Baker | |
| 2008/0167540 A1 | 7/2008 | Korhonen et al. | |
| 2008/0200775 A1 | 8/2008 | Lynn | |
| 2008/0249382 A1 | 10/2008 | Oh et al. | |
| 2008/0287815 A1 | 11/2008 | Chon et al. | |
| 2009/0163784 A1 | 6/2009 | Sarpeshkar et al. | |
| 2009/0247837 A1 | 10/2009 | Ochs et al. | |
| 2009/0306487 A1 | 12/2009 | Crowe et al. | |
| 2009/0306524 A1 | 12/2009 | Muhlsteff et al. | |
| 2009/0326349 A1 | 12/2009 | McGonigle | |
| 2009/0326395 A1 | 12/2009 | Watson | |
| 2009/0326831 A1 | 12/2009 | McGonigle | |
| 2010/0081897 A1 | 4/2010 | Li et al. | |
| 2010/0081899 A1 | 4/2010 | McKenna | |
| 2010/0113904 A1 | 5/2010 | Batchelder et al. | |
| 2010/0113908 A1 | 5/2010 | Vargas et al. | |
| 2010/0113909 A1 | 5/2010 | Batchelder et al. | |
| 2010/0174160 A1 | 7/2010 | Chance | |
| 2010/0286495 A1 | 11/2010 | McGonigle | |
| 2010/0292568 A1 | 11/2010 | Droitcour et al. | |
| 2010/0324389 A1 | 12/2010 | Moon et al. | |
| 2011/0021892 A1 | 1/2011 | Addison et al. | |
| 2011/0066062 A1 | 3/2011 | Banet et al. | |

(56) References Cited

U.S. PATENT DOCUMENTS

| | | |
|---|---|---|
| 2011/0071406 A1 | 3/2011 | Addison et al. |
| 2012/0232398 A1 | 9/2012 | Roham et al. |
| 2012/0253140 A1 | 10/2012 | Addison et al. |
| 2012/0296219 A1 | 11/2012 | Chon et al. |
| 2012/0310051 A1 | 12/2012 | Addison et al. |
| 2013/0137936 A1 | 5/2013 | Baker, Jr. et al. |
| 2013/0138002 A1 | 5/2013 | Weng et al. |
| 2013/0172767 A1 | 7/2013 | Dripps et al. |

FOREIGN PATENT DOCUMENTS

| | | |
|---|---|---|
| EP | 1507474 B1 | 2/2009 |
| WO | WO 00/21438 | 4/2000 |
| WO | WO 03/000125 A1 | 1/2003 |
| WO | WO 03/055395 A1 | 7/2003 |
| WO | WO 03/084396 A1 | 10/2003 |
| WO | WO 2004/075746 A2 | 9/2004 |
| WO | WO 2008/135985 A1 | 11/2008 |
| WO | WO 2009/043028 A2 | 4/2009 |
| WO | WO 2010/030238 A1 | 3/2010 |
| WO | WO 2010/135518 A1 | 11/2010 |
| WO | WO 2012/014065 A1 | 2/2012 |
| WO | WO 2012/051295 A2 | 4/2012 |

OTHER PUBLICATIONS

Rapaport and Cousin, "New phase-lock tracking instrument for foetal breathing monitoring," Med. & Biol. Eng. & Compo 1982, vol. 20, pp. 1-6.

Lindberg, L.G., Ughall, H., Oberg, PA, "Monitoring of respiratory and heart rates using a fibre-optic sensor," Medical & Biological Engineering & Computing, Sep. 1992. pages 533-537.

Long, S. "Phase Locked Loop Circuits." Apr. 27, 2005. https://web.archive.org/web/20081201083334/http://www.ece.ucsb.edu/~long/ece594a/PLL_intro594a_s05.pdf.

Lesurf, Jim. "FM & PM Demodulation." Oct. 2, 2007. https://web.archive.org/web/20071002193422/http://www.st-andrews.ac.uk/~www_pa/Scots_Guide/RadCom/part13/page1.html.

Addison, Paul S. et al., "Developing an Algorithm for Pulse Oximetry Derived Respiratory Rate (RRoxi): A Healthy Volunteer Study," Journal of Clinical Monitoring & Computing, 2012, 26: 45-51.

International Search Report and Written Opinion of the International Searching Authority for Application No. PCT/US2013/020338, mailed on Apr. 11, 2013. 6 pages.

International Search Report and Written Opinion of the International Searching Authority for Application No. PCT/US2014/014875, mailed on May 15, 2014. 6 pages.

International Search Report and Written Opinion of the International Searching Authority for Application No. PCT/US2014/014899, mailed on May 15, 2014. 6 pages.

Nguyen et al., "Comparison of two Methods for Demodulation of Pulse Signals—Application in Case of Central Sleep Apnea." *Journal of Science and Technology*, 49(1), 2011, pp. ISSN:0866-708X.

Supplementary European Search Report from the European Patent Office in European Patent Application No. 14749411, dated Aug. 10, 2016.

\* cited by examiner

600

602

| Patient: XYZ | Age | 42 |
| --- | --- | --- |
| Pulse Rate | 63 | Sex | M |
| Resp Rate | 12 | Sensor | 1 |
| Location | Finger | | |

606

- Light Exercise
- Strenuous Exercise ✓
- Sleep
- Anaesthetic
- Motion Artifacts
- Treatment 1
- Other

604

- High Blood Pressure ✓
- Heart Disease
- Pacemaker
- Arrhythmia
- Sleep Apnea
- Assisted Breathing
- Other

608

| Pulse Rate Variability | 10 | Pulse Amplitude Variability | 7 |
| --- | --- | --- | --- |
| Resp Rate Variability | 15 | Resp Amplitude Variability | 15 |

SYSTEMS AND METHODS FOR GENERATING AN ARTIFICIAL PHOTOPLETHYSMOGRAPH SIGNAL

The present disclosure relates to physiological signal processing, and more particularly relates to generating an artificial photoplethysmograph signal.

SUMMARY

A method for generating an artificial photoplethysmograph (PPG) signal comprises generating, using processing equipment, a frequency modulation component, an amplitude modulation component, and a baseline modulation component based on a respiratory profile. The method further comprises generating, using the processing equipment, a pulse signal based on a pulsatile profile and the frequency modulation component. The method further comprises modifying, using the processing equipment, the pulse signal based at least in part on the amplitude modulation component and the baseline modulation component to generate a respiration modulated signal. The method further comprises outputting the artificial PPG signal based at least in part on the respiration modulated signal.

A non-transitory computer-readable storage medium for providing an artificial photoplethysmograph (PPG) signal to an electronic device has a computer-readable medium having computer program instructions recorded thereon for generating a frequency modulation component, an amplitude modulation component, and a baseline modulation component based on a respiratory profile, generating a pulse signal based on a pulsatile profile and the frequency modulation component, modifying the pulse signal based at least in part on the amplitude modulation component and the baseline modulation component to generate a respiration modulated signal, and outputting the artificial PPG signal based at least in part on the respiration modulated signal.

A test unit comprises processing equipment configured to generate a frequency modulation component, an amplitude modulation component, and a baseline modulation component based on a respiratory profile, generate a pulse signal based on a pulsatile profile and the frequency modulation component, modify the pulse signal based at least in part on the amplitude modulation component and the baseline modulation component to generate the artificial PPG signal and output the artificial PPG signal.

BRIEF DESCRIPTION OF THE FIGURES

The above and other features of the present disclosure, its nature and various advantages will be more apparent upon consideration of the following detailed description, taken in conjunction with the accompanying drawings in which:

FIG. 6 shows an illustrative parameter selection interface in accordance with some embodiments of the present disclosure;

DETAILED DESCRIPTION OF THE FIGURES

Figure 1:
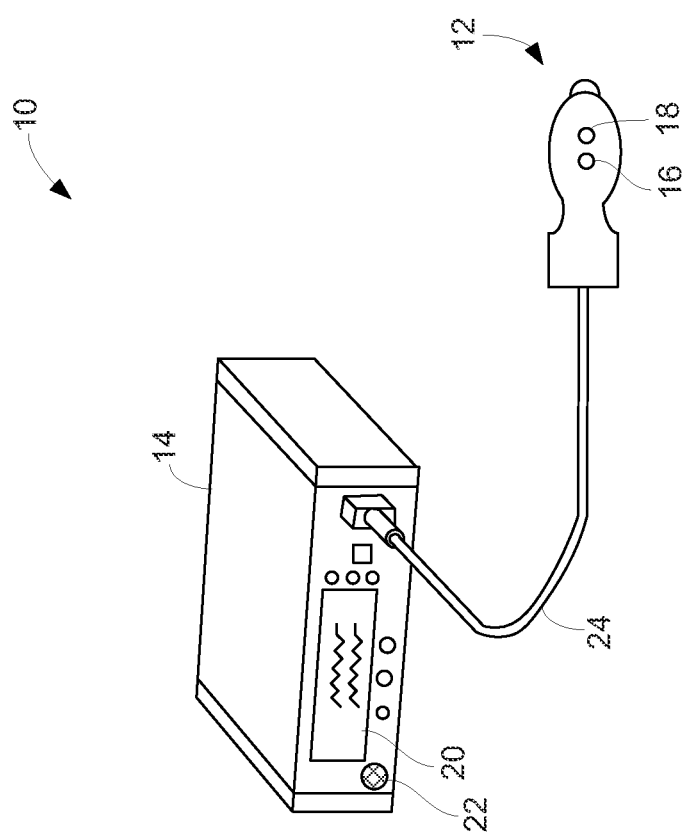
FIG. 1 shows an illustrative patient monitoring system in accordance with some embodiments of the present disclosure.

A pulse oximeter may include a pulse oximetry sensor device that includes LEDs that generate light that passes through blood perfused tissue. A detector detects the light after it has been passed through the tissue and generates a photoplethysmograph (PPG) signal that is provided to a pulse oximetry monitor, which processes the PPG signal as a representation of the intensity of the received light over time. The PPG signal may generally represent pulsatile blood flow through the tissue, which may vary based on a number of physiological and non-physiological factors. Physiological factors that impact the PPG signal may include pulsatile factors (e.g., heart beat and blood pressure) and respiratory factors (e.g., breathing). Non-physiological factors may include patient characteristics (e.g., patient age and sensor location) and environmental factors (e.g., sensor type, sensor location, and motion artifacts).

It may be desirable to generate an artificial PPG signal, for example, for equipment testing and diagnostic purposes, for comparison to real clinical data, for research purposes, or for any other suitable purpose. For purposes of brevity and clarity, the present disclosure is described in the context of using the artificial PPG signal as a PPG test signal. Given the large number of factors that impact the PPG signal, a particular artificial PPG signal may not be representative of the complete patient population, a diversity of patient physiological conditions, or differing measurement conditions.

In an exemplary embodiment, a test unit may include processing equipment for generating an artificial PPG signal (e.g., a PPG test signal) based on one or more profiles. For example, a PPG test signal may be generated based on a pulsatile profile, a respiratory profile, a patient profile, an artifact profile, any other suitable profile, or any combination thereof. The PPG test signal may be changed by modifying any of the underlying profiles.

For purposes of clarity, the present disclosure is written in the context of the physiological signal being a PPG signal generated by a pulse oximetry system, and an artificial physiological signal being an artificial PPG signal or PPG test signal. It will be understood that any other suitable artificial physiological signal may be generated in accordance with the teachings of the present disclosure.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_0$=intensity of light transmitted;
S=oxygen saturation;
$\beta_o$, $\beta_r$-empirically derived absorption coefficients; and l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of EQ. 1 is taken ("log" will be used to represent the natural logarithm) for IR and Red to yield $$\log I = \log I_o - (s\beta_o + (1-s)\beta_r)l. \quad (2)$$

2. Eq. 2 is then differentiated with respect to time to yield.

$$\frac{d\log I}{dt} = -(s\beta_o + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})}. \quad (4)$$

4. Solving for S yields $$s = \frac{\frac{d\log I(\lambda_{IR})}{dt}\beta r(\lambda_R) - \frac{d\log I(\lambda_R)}{dt}\beta r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}. \quad (5)$$

5. Note that, in discrete time, the following approximation can be made:

$$\frac{d\log I(\lambda, t)}{dt} \simeq \log I(\lambda, t_2) - \log I(\lambda, t_1). \quad (6)$$

6. Rewriting Eq. 6 by observing that log A−log B=log (A/B) yields $$\frac{d\log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."

8. Solving Eq. 4 for S using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{dI/dt}{I}, \qquad (10)$$

Eq. 8 becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \qquad (11)$$

$$= \frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$

$$= R.$$

which defines a cluster of points whose slope of y versus X will give R when $$x=[I(t_2,\lambda_{IR})-I(t_1,\lambda_{IR})]I(t_1,\lambda_R), \qquad (12)$$

and $$y=[I(t_2,\lambda_R)-I(t_1,\lambda_R)]I(t_1,\lambda_{IR}). \qquad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light, at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to some embodiments, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation (e.g., $SpO_2$), and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may allow communication between monitor 14 and sensor unit 12.

As is described herein, monitor 14 may generate a PPG signal based on the signal received from sensor unit 12. The PPG signal may consist of data points that represent a pulsatile waveform. The pulsatile waveform may be modulated based on the respiration of a patient. Respiratory modulations may include baseline modulations, amplitude modulations, frequency modulations, respiratory sinus arrhythmia, any other suitable modulations, or any combination thereof. Respiratory modulations may exhibit different phases, amplitudes, or both, within a PPG signal and may contribute to complex behavior (e.g., changes) of the PPG signal. For example, the amplitude of the pulsatile waveform may be modulated based on respiration (amplitude modulation), the frequency of the pulsatile waveform may be modulated based on respiration (frequency modulation), and a signal baseline for the pulsatile waveform may be modulated based on respiration (baseline modulation). Monitor 14 may analyze the PPG signal (e.g., by demodulating the PPG signal) to determine respiration information based on one or more of these modulations of the PPG signal.

As is described herein, respiration information may be determined from the PPG signal by monitor 14. However, it will be understood that the PPG signal could be transmitted to any suitable device for the determination of respiration information, such as a local computer, a remote computer, a nurse station, mobile devices, tablet computers, or any other device capable of sending and receiving data and performing processing operations. Information may be transmitted from monitor 14 in any suitable manner, including wireless (e.g., WiFi, Bluetooth, etc.), wired (e.g., USE, Ethernet, etc.), or application-specific connections. The receiving device may determine respiration information as described herein.

Figure 2:
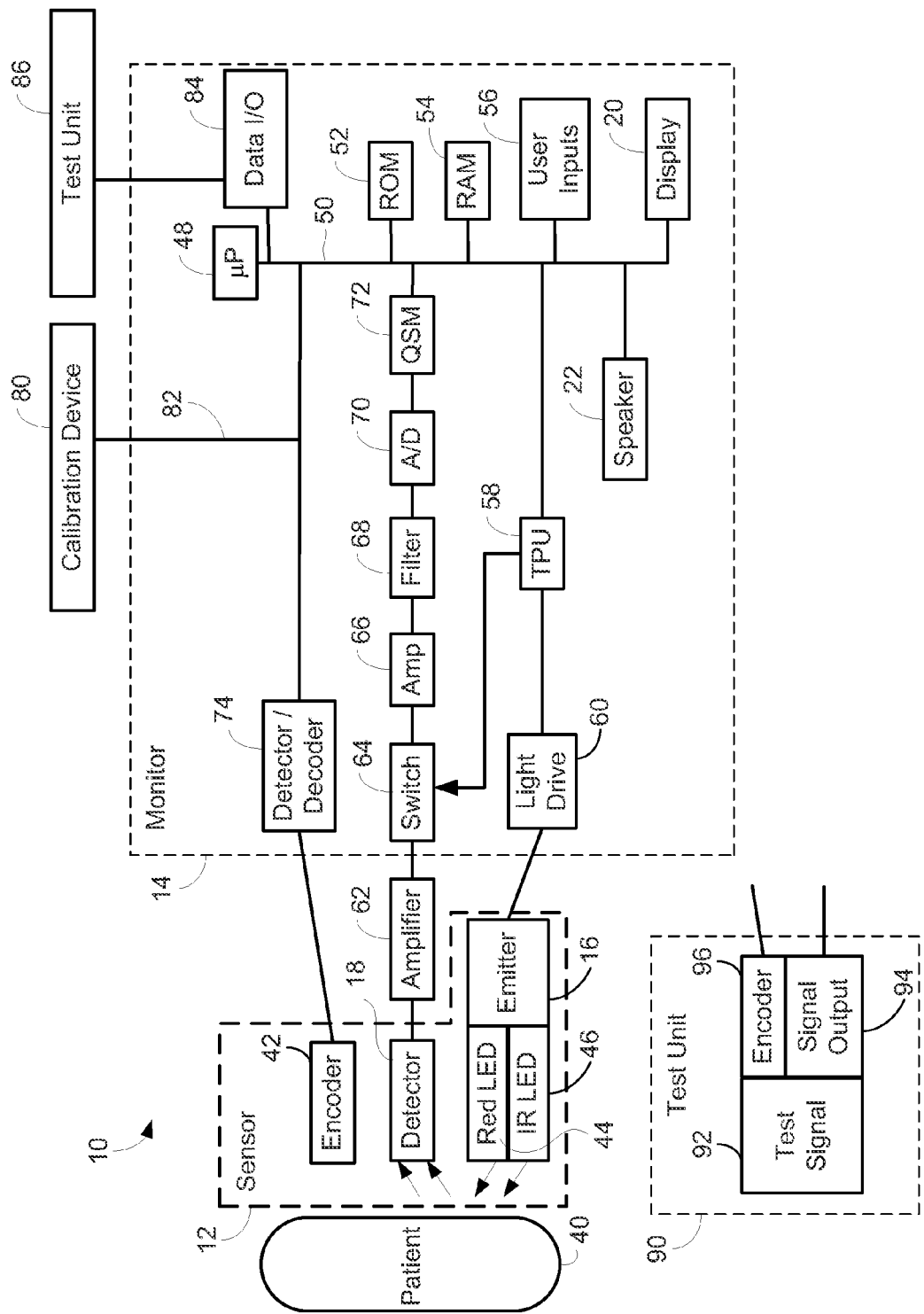
FIG. 2 is a block diagram of the illustrative patient monitoring system of FIG. 1 coupled to a patient and a test unit in accordance with some embodiments of the present disclosure.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42.

Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics and treatment information. In some embodiments, encoder 42 may include a memory on which one or more of the following information may be stored for communication to monitor 14; the type of the sensor unit 12; the wavelengths of light emitted by emitter 16; the particular wavelength each sensor in the sensor array is monitoring; a signal threshold for each sensor in the sensor array; any other suitable information; physiological characteristics (e.g., gender, age, weight); or any combination thereof.

In some embodiments, sensor unit 12 may be replaced with a test unit 90. In an exemplary embodiment, test unit 90 may include a test signal generator 92, a signal output 94, and an encoder 96. Test signal generator 92 may generate a PPG test signal (e.g., as described in FIGS. 3, 8, 9, and 10) that may approximate a PPG signal that would be generated by a passing light through a patient's tissue. Signal output 94 may convert the samples of the PPG test signal to one or more electrical signals that are provided to monitor 12 (e.g., through amplifier 62). In this manner, a test signal generated by the test unit 90 may be provided to monitor 14. In some embodiments, the signal provided by test unit 90 may simulate one (Red or IR) signal typically received at monitor 14, while in other embodiments the signal provided by test unit 90 may simulate both the Red and IR signals. In some embodiments, encoder 96 may store information similar to encoder 42. The settings for information stored in encoder 96 may be programmable to allow system parameters to be modified, for example, based on one or more profiles as described herein.

In some embodiments, signals from detector 18 (or signal output 94) and encoder 42 for encoder 96) may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18 (or generated by signal output 94). As is described herein, microprocessor 48 may utilize amplitude demodulation and/or frequency demodulation techniques to determine respiration information from a PPG signal.

Signals corresponding to information about patient 40, and particularly about the intensity of light emanating from a patients tissue over time, may be transmitted from encoder 42 (or encoder 96) to decoder 74. These signals may include, for example, encoded information relating to patient characteristics. Decoder 74 may translate these signals to enable microprocessor 48 to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Data input/output (I/O) 84 may provide for communications with other devices utilizing any suitable transmission medium, including wireless (e.g., WiFi, Bluetooth, etc.), wired (e.g., USE, Ethernet, etc.), or application-specific connections. Data I/O 84 may receive messages to be transmitted from microprocessor 48 via bus 50. Exemplary messages to be sent in an embodiment described herein may include samples of the PPG signal to be transmitted to an external device for determining respiration information. Data I/O 84 may also receive messages from an external device to be transmitted to microprocessor 48 via bus 50.

In an another exemplary embodiment of a test unit connecting to monitor 14, test unit 86 may connect to monitor 14 through data I/O 84. Test unit 86 may generate a PPG test signal (e.g., as described in FIGS. 3, 8, 9, and 10) that may approximate a PPG signal that would be generated by passing light through a patient's tissue. In the exemplary embodiment of test unit 86, the PPG test signal may be a set of samples similar to what would be provided to microprocessor 48 through the detection circuitry (e.g., switch 64, amplifier 66, filter 68, A/D converter 70, and QSM 72) of monitor 14.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
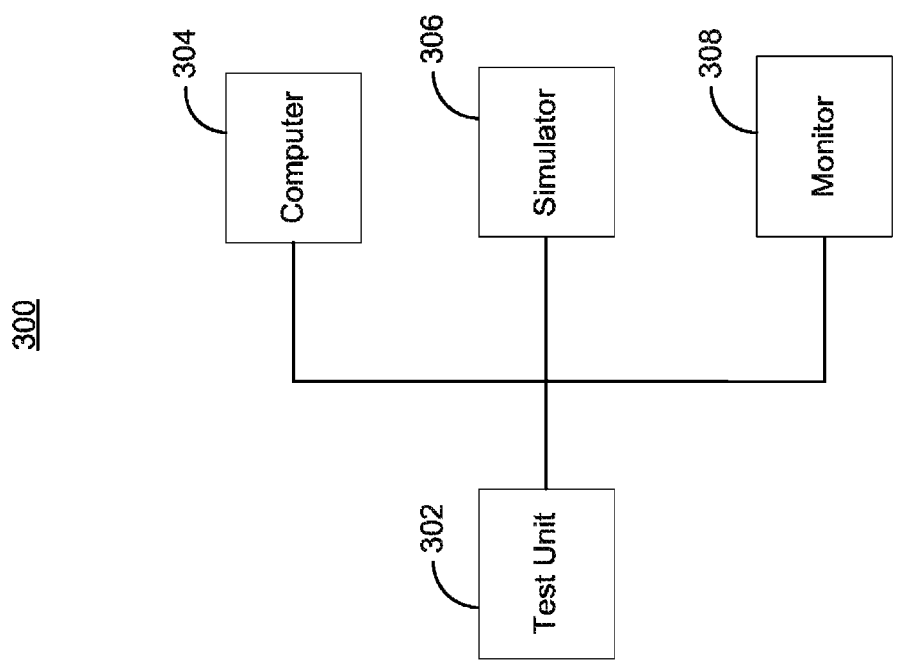
FIG. 3 shows an illustrative test unit for generating a PPG test signal in accordance with some embodiments of the present disclosure.

FIG. 3 shows an illustrative embodiment of a test unit 302 in accordance with some embodiments of the present disclosure. Although a test unit 302 may be implemented in any suitable manner, in an exemplary embodiment test unit 302 may be a general purpose computer (e.g., a personal computer). In other embodiments, test unit 302 may be implemented as an application-specific embedded device. It will be understood that any suitable computing device may perform the functionality of test unit 302, such as a tablet computer, smart phone, nurse station, physiological monitor, or any other suitable electronic device. It will be understood that any functionality of test unit 302 (e.g., as described in FIGS. 8, 9, and 10) may be implemented in hardware, software, or both hardware and software.

Although test unit 302 may communicate with any suitable electronic device, or be integrated into any suitable electronic device, in exemplary embodiments test unit 302 may be in communication with a computer 304, simulator 306, or monitor 308. Test unit 302 may communicate with electronic devices in any suitable manner, including wireless (e.g., WIFi, Bluetooth, etc.), wired (e.g., USE, Ethernet, etc.), or application-specific connections such as a connection that simulates the output of a sensor (e.g., test unit 90 of FIG. 2).

Test unit 302 may include a user interface such as a keyboard or touch screen to allow a user to input, select, or modify parameters related to generating a PPG test signal (e.g., as depicted in FIG. 6). Although any suitable parameters may be used to generate a PPG test signal, in an exemplary embodiment, a PPG test signal may be based upon one or more of a pulsatile profile, a respiratory profile, a patient profile, and an artifact profile, any other suitable profile, or any combination thereof. In some embodiments, test unit 302 may include an analysis or simulator program. An analysis or simulator program may display simulated PPG waveforms based on a PPG test signal, calculate simulated physiological parameters (e.g., pulse rate, oxygen saturation, respiration information, and/or blood pressure) based on a PPG test signal, or perform any other suitable processing operations.

In some embodiments test unit 302 may communicate with a computer 304, for example, to transmit the PPG test signal to computer 304. Although a computer 304 is described, it will be understood that any suitable computing device (e.g., a tablet computer or smart phone) may be used in accordance with the embodiments described herein. In an exemplary embodiment test unit 302 may generate a PPG signal and transmit data representing the PPG signal to computer 304. Computer 304 may display simulated PPG waveforms based on a PPG test signal, calculate simulated physiological parameters (e.g., pulse rate, oxygen saturation, respiration information, and/or blood pressure) based on the PPG test signal, or perform any other suitable processing operations. In other embodiments, computer 304 may utilize the PPG test signal to test algorithms that process a PPG signal.

In some embodiments test unit 302 may communicate with a simulator 306, for example, to transmit the PPG test signal to simulator 306. A simulator 306 may be a device that is configured to generate a simulated PPG waveform based on receiving input data describing a simulated PPG waveform. In some embodiments, simulator 306 may display the simulated PPG waveform and calculate physiological parameters based on the received data. In other embodiments, simulator 306 may generate a simulated PPG waveform for output to another device such as a patient monitor, a computer, or both.

In some embodiments, test unit 302 may communicate with a monitor 308 such as monitor 14, for example, to transmit the PPG test signal to monitor 308. As is described herein, test unit 302 may communicate with monitor 308 in any suitable manner, including through a data I/O port of a monitor 308 (e.g., test unit 86 communicating through data I/O 84 in FIG. 2) or by simulating a detected sensor signal (e.g., as described for test unit 90 in FIG. 2). In some embodiments, the test unit may include or may be connected to circuitry or a device that generates a signal that approximates the output of a sensor such as sensor 12 based on a set of samples of the PPG test signal. Although it will be understood that any suitable circuitry or device may be used, in an exemplary embodiment the signal may be generated by the SRC-MAX manufactured by Nellcor, Inc.

Figure 4:
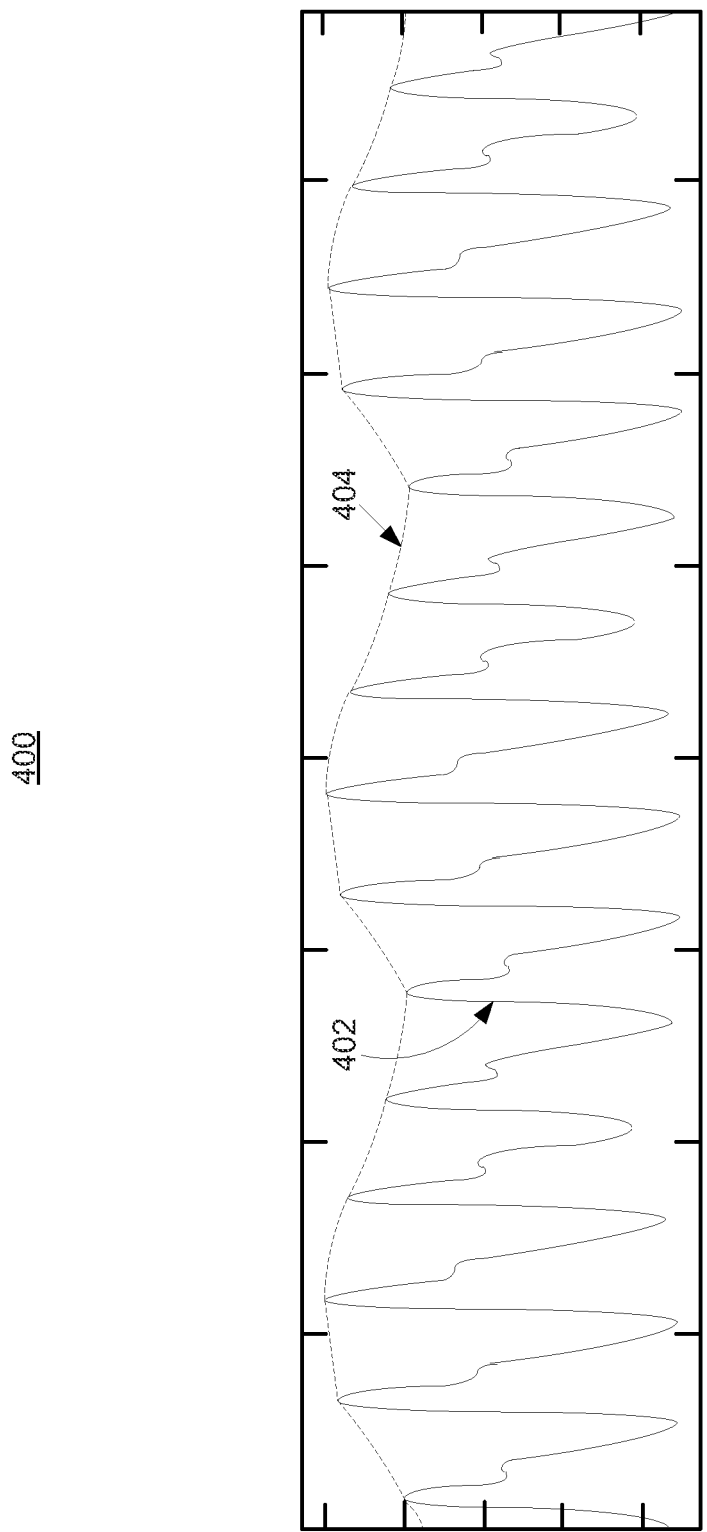
FIG. 4 shows an illustrative amplitude modulated PPG signal in accordance with some embodiments of the present disclosure.

FIG. 4 shows an illustrative amplitude modulated PPG signal in accordance with some embodiments of the present disclosure. A PPG signal may demonstrate multiple modulations based on the respiration of a patient, such as amplitude modulation, frequency modulation, and baseline modulation. FIG. 4 depicts a PPG signal including at least an amplitude modulation component of the PPG signal due to respiration. PPG signal 402 may be a periodic signal that is indicative of changes in pulsatile blood flow. Each cycle of PPG signal 402 may generally correspond to a pulse, such that a heart rate may be determined based on PPG signal 402.

The volume of the pulsatile blood flow may also vary in a periodic manner based on respiration. The period of a respiratory cycle may typically be longer than the period of a pulsatile cycle, such that any changes in the pulsatile blood flow due to respiration occur over a numb of pulsatile cycles. As one example of changes in pulsatile blood flow due to respiration, the amplitude of PPG signal 402 may be modulated based on respiration. In the exemplary embodiment depicted in FIG. 4, the amplitude of the pulsatile blood flow depicted by PPG signal 402 may vary based on a respiratory cycle caused by an amplitude modulation component 404.

Although it will be understood that the respiratory amplitude modulation component 404 may impact the amplitude of PPG signal 402 differently based on patient conditions, measurement location, or in other manners, in the exemplary embodiment of FIG. 4, the amplitude of PPG signal 402 varies in a generally uniform manner based on a respiratory cycle. Each cycle of respiratory amplitude modulation component 404 may correspond to a breath. For example, as is depicted in FIG. 4, a single breath may occur approximately once for every five pulsatile cycles (e.g., heart beats). Accordingly, a respiration rate corresponding to respiratory amplitude modulation component 404 may be at approximately one fifth of the rate of the pulse rate associated with PPG signal 402. As will be described herein, a PPG test signal may be generated based at least in part on an amplitude modulation signal that is related to the amplitude modulation component 404 of PPG signal 402.

Figure 5:
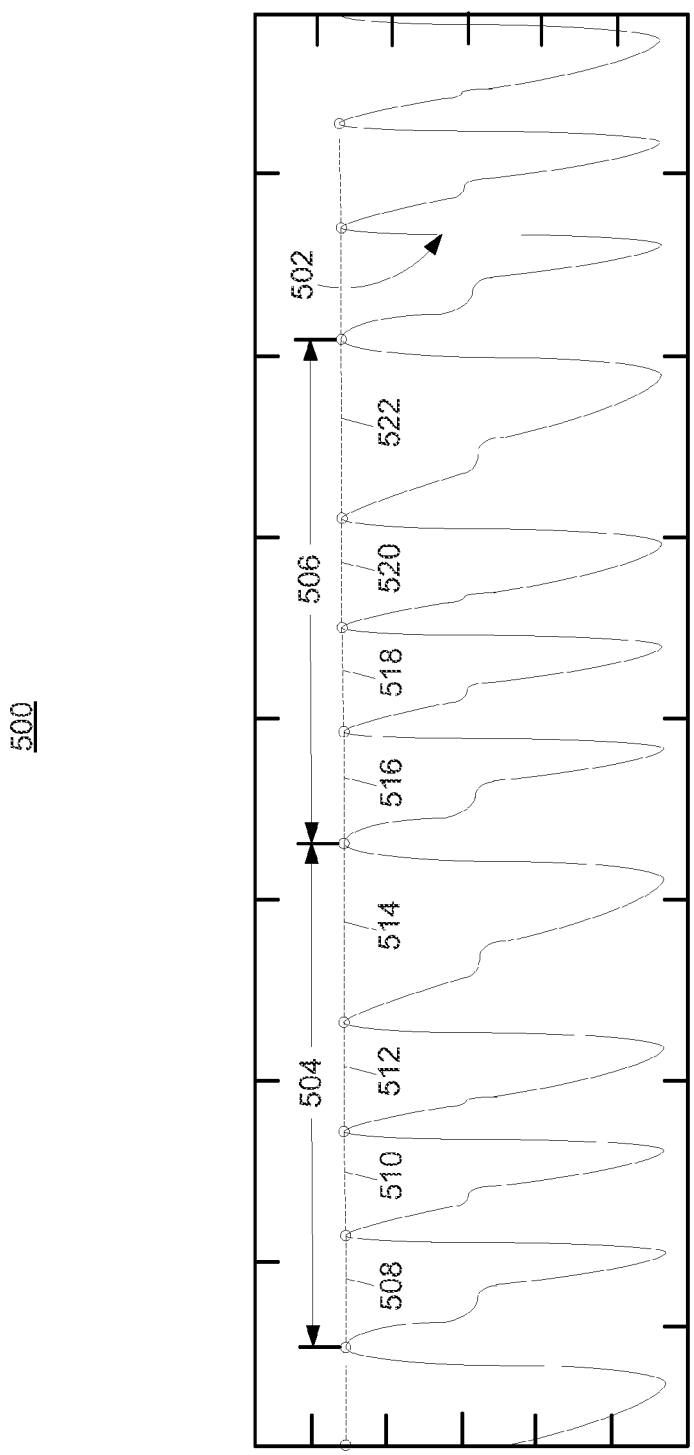
FIG. 5 shows an illustrative frequency modulated PPG signal in accordance with some embodiments of the present disclosure.

FIG. 5 shows an illustrative frequency modulated PPG signal in accordance with some embodiments of the present disclosure. FIG. 5 depicts a PPG signal 502 including at least a frequency modulation component of the PPG signal due to respiration. PPG signal 502 may be a periodic signal that is indicative of changes in pulsatile blood flow. Each cycle of PPG signal 502 may generally correspond to pulse, such that a heart rate may be determined based on the frequency of PPG signal 502.

The timing of the pulsatile blood flow may vary in a periodic manner based on respiration. The period of a respiratory cycle may typically be longer than the period of a pulsatile blood cycle, such that any changes in the pulsatile blood flow due to respiration occur over a number of pulsatile cycles. As one example of changes in pulsatile blood flow due to respiration, the phase and frequency of PPG signal 502 may be modulated based on respiration. In the exemplary embodiment depicted in FIG. 5, the timing, frequency, and period associated with each pulsatile cycle may vary based on a respiratory cycle caused by a frequency modulation component (e.g., 504, 506).

In an exemplary embodiment, a series of pulses may have a relatively uniform pulse period in the absence of frequency modulation (not depicted). Although it will be understood that the frequency modulation of PPG signal 502 may impact the phase and frequency of PPG signal 502 differently based on patient conditions, measurement location, or in other manners, in the exemplary embodiment of FIG. 5 the pulse period associated with individual pulses may vary in a generally uniform manner based on the relative timing of pulses within a respiratory cycle. For example, respiratory cycles 504 and 506 may each correspond to a breath of a patient, and a respiration rate at approximately one fourth of the pulse rate. The pulsatile flow of PPG signal 502 may vary such that the period of each pulse is altered based on the relative location within the respiratory cycle, as depicted by pulse periods 508, 510, 512, 514, 516, 518, 520, and 522. As will be described herein, a PPG test signal may be generated based in part on an amplitude modulation signal that is related to the frequency modulation (e.g., 504 and 506) of PPG signal 502.

FIG. 6 is an illustrative block diagram of a parameter selection interface 600 as described herein. As will be described herein, the PPG test signal may be generated based on one or more profiles such as a pulsatile profile, a respiratory profile, a patient profile, and an artifact profile. Although a number of particular profiles are described herein, it will be understood that any suitable profile may be provided for generating a PPG test signal. The profiles described herein are not mutually exclusive, and may be combined or modified in any suitable manner.

In some embodiments, a user may modify aspects of one or more profiles using parameter selection interface 600. Although the profiles may be modified in any suitable manner, in an exemplary embodiment, a user may select or enter a set of patient characteristics, such as a heart rate pattern, a respiration rate pattern, patient age, measurement conditions (e.g., under medication or while exercising), measurement equipment (e.g., sensor and pulse oximeter type) or any other suitable characteristics relating to a patient. Each of the profiles may be generated based on these characteristics. In some embodiments each of the profiles may be modified directly, for example, by directly modifying one or more variables relating to the PPG signal such as heart rate, dichrotic notch location, respiration rate, respiratory amplitude modulation, respiratory frequency modulation, respiratory baseline modulation, patient transmissivity, patient perfusion, and artifact patterns. In some embodiments, the profiles may be modified based on an analysis of inputs to the parameter selection interface. For example, a user may select one or more activity or data patterns to modify the modulation components that are generated based on the profiles. For example, activity patterns may be created that introduce predetermined or random changes to the values of any of the profile values over time, for example, based on known physical activity patterns, treatment regimens, or physiological conditions. Although in an exemplary embodiment the profiles are described as being acquired in a particular order (i.e., steps 802-808 of FIG. 8), it will be understood that the profiles could be acquired in any other order, could be acquired in parallel, or could be acquired in any other suitable manner.

An exemplary parameter selection interface 600 may include a patient information section 602, a physical condition section 604, a measurement and treatment section 606, and a parameter section 608. Although an exemplary configuration of a parameter selection interface 600 is described herein, it will be understood that parameter selection interface 600 could be configured in any suitable manner, could include any number of configuration screens, and could include any number or configuration of possible selections for generating one or more profiles.

Patient information section 602 may include basic information related to a patient and relevant health parameters. Although any suitable information may be included in patient information section 602, in an exemplary embodiment patient information section 602 may include information such as patient name, age, sex, pulse rate, respiration rate, sensor type, and sensor location. These values may be used to generate one or more profiles, such as a pulsatile profile (e.g., based in part on pulse rate) and a respiratory profile (e.g., based in part on respiration rate). Although values for patient information section 602 may be selected in any suitable manner, in an exemplary embodiment values for patient name, pulse rate, respiration rate, and age may be entered manually (e.g., through a keyboard or touch screen) while the values for the patient sex, sensor type, and sensor location may be selected from a menu.

Physical condition section 604 may include information related to physical conditions that may impact the shape of the PPG test signal, and therefore impact one or more profiles. For example, conditions related to heart health or blood circulation (e.g., blood pressure, heart disease, a pacemaker, or arrhythmia) may impact one or more profiles such as the pulsatile profile, while other conditions (e.g., sleep apnea or assisted breathing) may impact one or more other profiles such as a respiratory profile. It will be recognized that any suitable physical conditions may be selected within physical condition section 604. In an exemplary embodiment, an "other" category may allow for additional physical conditions to be selected based on an associated profile that is provided to the system. Although physical conditions within physical condition section 604 may be selected in any suitable manner, in an exemplary embodiment one or more physical conditions may be selected from a list.

Measurement and treatment section 606 may include information related to measurement conditions or patient treatments that may impact the shape of the PPG test signal, and therefore impact one or more profiles. For example, conditions related to physical activity (e.g., exercise, sleep, or motion artifact) and conditions related to treatments (e.g., anaesthetic or treatment 1) may impact a pulsatile profile, respiratory profile, patient profile and artifact profile. It will be recognized that any suitable measurement conditions or patient treatments may be selected within measurement and treatment section 606. In an exemplary embodiment, the "treatment 1" and "other" categories may allow for additional treatments or physical activity profiles to be selected based on an associated profile that is provided to the system. Although measurement conditions and patient treatments within measurement and treatment section 606 may be selected in any suitable manner, in an exemplary embodiment one or more measurement conditions or patient treatments may be selected from a list.

Parameter section 608 may include information to allow the variability of the waveform to be modified to reflect physical conditions changing over time. Although any parameters may be included in parameter section. 608, in an exemplary embodiment parameter section 608 may include percentage values for pulse rate variability, pulse amplitude variability, respiration rate variability, and respiration amplitude variability to be modified. These values may be used to generate one or more profiles, such as a pulsatile profile (e.g., based on pulse rate variability and pulse amplitude variability), respiratory profile (e.g., based on respiration rate variability and respiration amplitude variability), patient profile, and artifact profile. Although values for parameter section 608 may be selected in any suitable manner, in an exemplary embodiment values for pulse rate variability, pulse amplitude variability, respiration rate variability, and respiration amplitude variability age may be entered manually (e.g., through a keyboard or touch screen).

Figure 7:
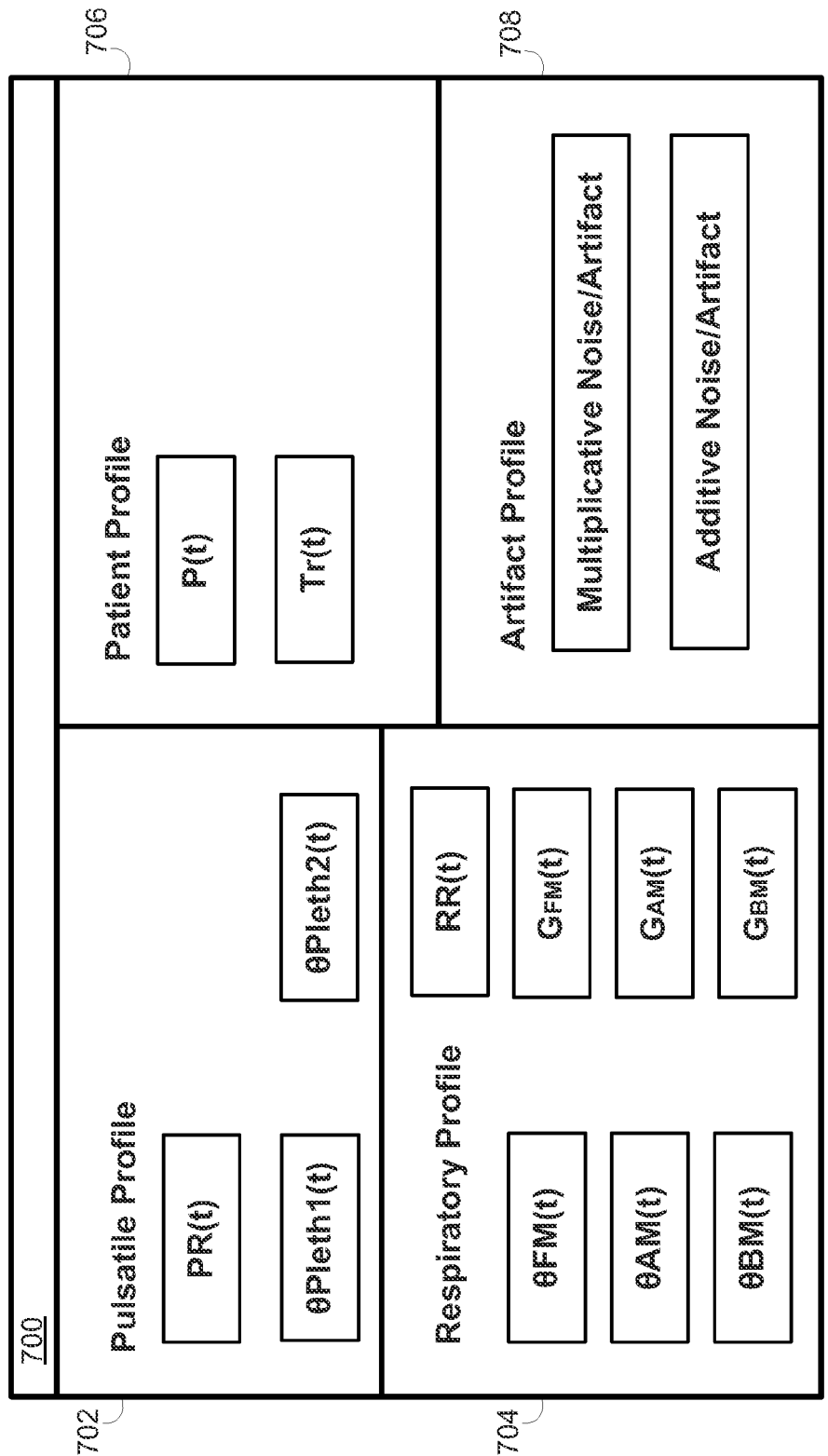
FIG. 7 shows illustrative profiles in accordance with some embodiments of the present disclosure.

FIG. 7 depicts illustrative profiles in accordance with some embodiments of the present disclosure. Although profiles may be generated in any suitable manner, in an exemplary embodiment profiles may be generated based on selections made using parameter selection interface 600. Although any suitable profiles may be generated, in an exemplary embodiment the profiles may include a pulsatile profile 702, a respiratory profile 704, a patient profile 706, and an artifact profile 708. Although a pulsatile profile 702 may include any suitable profile characteristics, in an exemplary embodiment the pulsatile profile may include a pulse rate pattern PR(t), a first pulsatile component phase $\theta_{PLETH1}(t)$, and a second pulsatile component phase $\theta_{PLETH2}(t)$. Although a respiratory profile 704 may include any suitable profile characteristics, in an exemplary embodiment the respiratory profile may include a respiration rate pattern RR(t), a frequency modulation phase $\theta FM(t)$, an amplitude modulation phase $\theta AM(t)$, a baseline modulation phase $\theta BM(t)$, a frequency modulation gain $G_{FM}(t)$, an amplitude modulation gain $G_{AM}(t)$, and a baseline modulation gain $G_{AM}(t)$. Although a patient profile 706 may include any suitable profile characteristics, in an exemplary embodiment the respiratory profile may include a perfusion signal P(t) and a transmissivity signal Tr(t). Although an artifact profile 708 may include any suitable profile characteristics, in an exemplary embodiment the respiratory profile may include multiplicative artifacts and additive artifacts.

Figure 8:
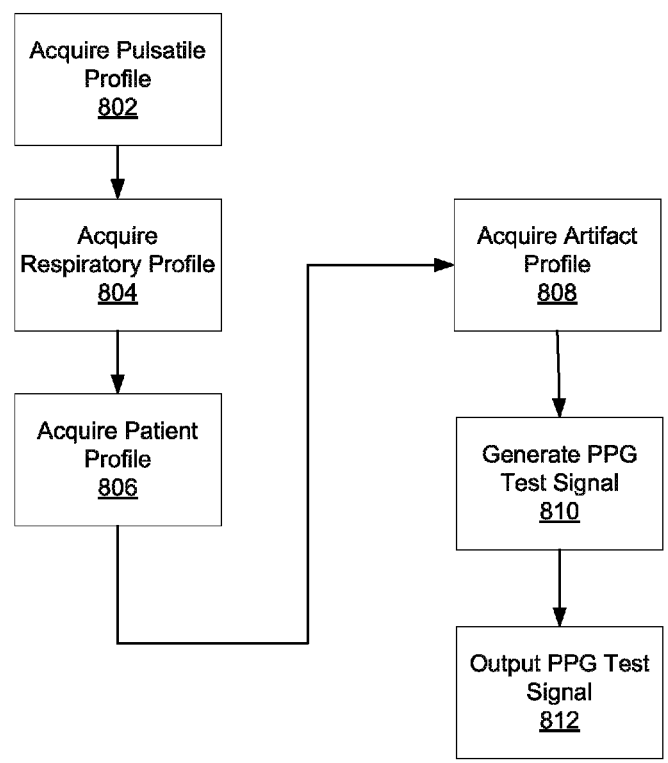
FIG. 8 is a flow diagram showing illustrative steps for generating a PPG test signal in accordance with some embodiments of the present disclosure.

FIG. 8 is a flow diagram showing illustrative steps for generating a PPG test signal in accordance with some embodiments of the present disclosure. At step 802, test unit 302 may acquire a pulsatile profile (e.g., that is generated based on values entered in parameter selection interface 600). The pulsatile profile may include any suitable information relating to generating a pulsatile component of a PPG test waveform, such as a waveform shape, pulse rate, or both. Although a pulsatile profile may be acquired in any suitable manner, in an exemplary embodiment aspects of the pulsatile profile may be stored in memory and aspects of the pulsatile profile may be provided by a user. For example, in some embodiments a user may select between multiple pulsatile profiles based on desired characteristics of the PPG test signal (e.g., whether the PPG test signal simulates a neonate or an adult) or based on known physiological conditions or treatments (e.g., exercise patterns, high blood pressure, arrhythmia, or use of a bronchodilator drug by an asthmatic patient). In other embodiments the user may modify the pulsatile profile, for example, to modify a pulse rate associated with the PPG test signal.

At step 804, test unit 302 may acquire a respiratory profile (e.g., that is generated based on values entered in parameter selection interface 600). The respiratory profile may include any suitable information relating to respiratory modifications to the pulsatile component of a PPG test waveform, such as amplitude modulation, frequency modulation, baseline modulation, respiration rate, or any combination thereof. Although a respiratory profile may be acquired in any suitable manner, in an exemplary embodiment aspects of the respiratory profile may be stored in memory and aspects of the respiratory profile may be provided by a user. For example, in some embodiments a user may select between multiple respiratory profiles based on desired characteristics of the PPG test signal (e.g., whether the PPG test signal simulates a neonate or an adult) or known physiological conditions or treatments (e.g., exercise patterns, sleep apnea, or assisted breathing) In other embodiments the user may modify the respiratory profile, for example, to modify a respiratory rate associated with the PPG test signal.

At step 806, test unit 302 may acquire a patient profile (e.g., that is generated based on values entered in parameter selection interface 600). The patient profile may include additional suitable information relating to modifications to a PPG test waveform based on patient characteristics such as age, skin type, measurement location, sensor type, sensor location, or any combination thereof. Although a patient profile may be acquired in any suitable manner, in an exemplary embodiment aspects of the patient profile may be stored in memory and aspects of the patient profile may be provided by a user. For example, in some embodiments a user may select between multiple patient profiles based on desired characteristics of the PPG test signal (e.g., whether the PPG test signal simulates a neonate or an adult) or known measurement conditions (e.g., to simulate noisy measurement conditions, different sensor types, or sensor locations). In other embodiments the user may modify the patient profile, for example, to select a particular simulated measurement location or sensor type associated with the PPG test signal.

At step 808, test unit 302 may acquire an artifact profile (e.g., that is generated based on values entered in parameter selection interface 600). The artifact profile may include additional information relating to modifications to a PPG test waveform based on artifacts such as motion artifacts. Although an artifact profile may be acquired in any suitable manner, in an exemplary embodiment aspects of the artifact profile may be stored in memory and aspects of the artifact profile may be provided by a user. For example, in some embodiments an artifact profile may be generated based on known conditions that result in artifacts (e.g., improper sensor placement or patient motion).

At step 810, test unit 302 may generate the PPG test signal. Although the PPG test signal may be generated in any suitable manner, in an exemplary embodiment the PPG test signal may be generated as described in FIGS. 9 and 10, described below. At step 812, test unit 302 may output the PPG test signal. Although the PPG test signal may be output in any suitable manner to any suitable device, in exemplary embodiments the PPG test signal may be provided as a data signal to other processing circuitry of test unit 302 (e.g., a test program running on test unit 302), a remote computing device 304 (e.g., a computer, tablet, or smart phone), a simulator 306, a patient monitor 308, or any other suitable device.

Figure 9:
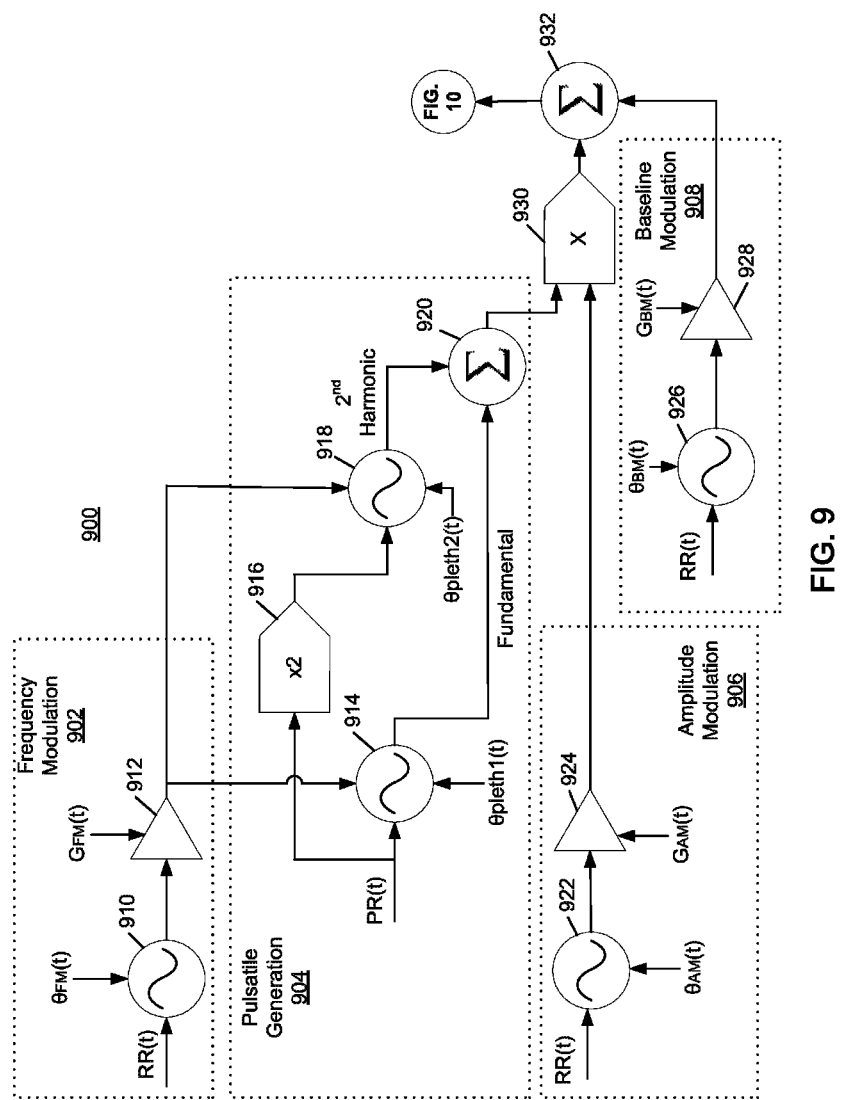
FIG. 9 is a flow diagram showing an illustrative flow for generating a PPG test signal in accordance with some embodiments of the present disclosure.
Figure 10:
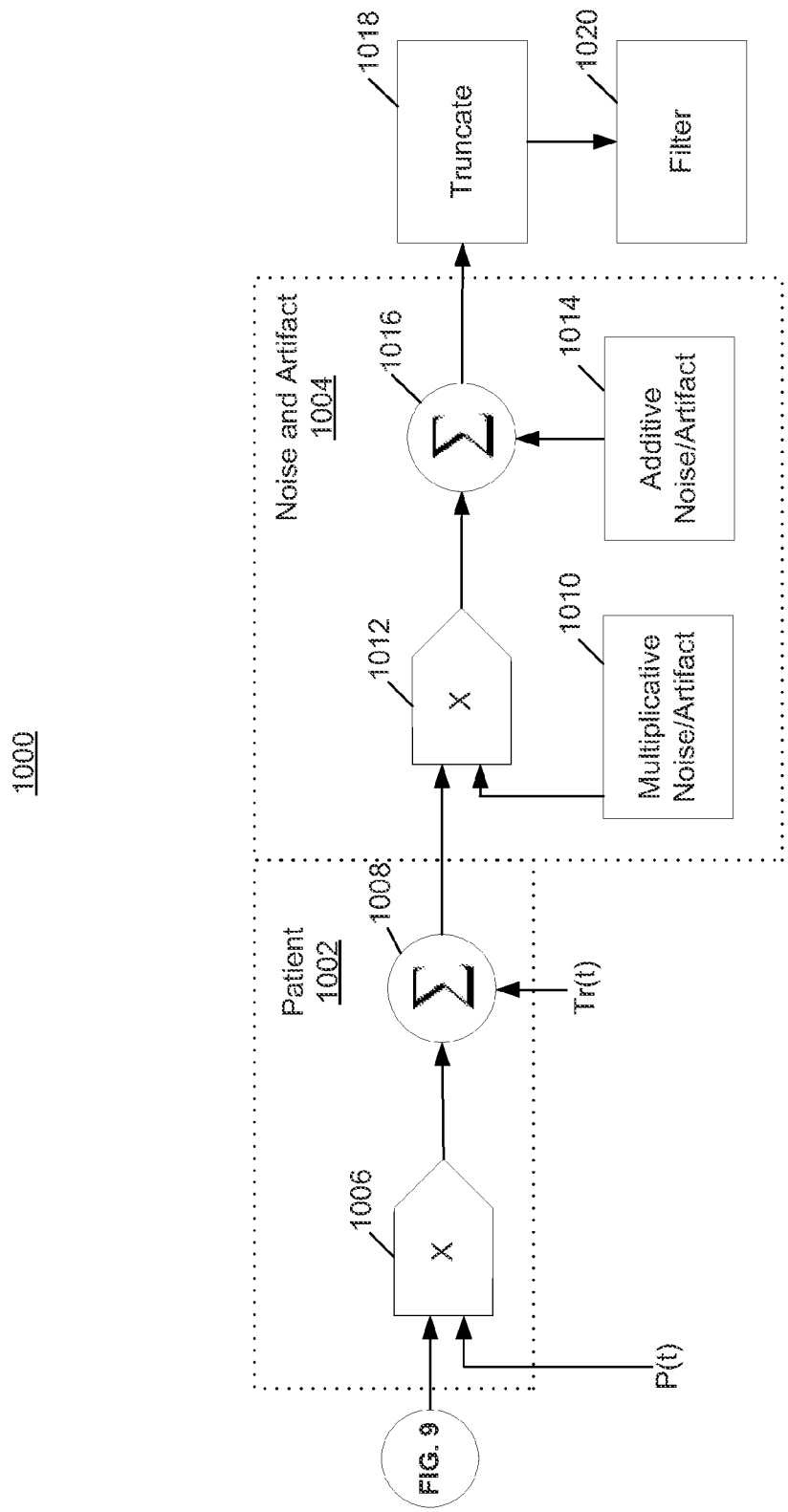
FIG. 10 is a flow diagram showing an illustrative flow for generating a PPG test signal in accordance with some embodiments of the present disclosure.

FIGS. 9 and 10 are signal flow diagrams showing an illustrative flow for generating a PPG test signal in accordance with some embodiments of the present disclosure. Although a particular flow is depicted and described in FIGS. 9 and 10, it will be understood that the order of the flow may be modified, that additional procedures may be performed or inserted at any point in the flow, and that aspects of the flow may be omitted in any suitable manner. The flow depicted in FIGS. 9 and 10 includes processing equipment for performing signal processing operations such as signal generators, multipliers, adders, amplifiers, and other processing equipment. It will be understood that each signal processing operation may be implemented in any suitable manner, including hardware, software, hardware and software, discreet circuitry, application-specific circuitry, or any combination thereof.

The flow depicted in FIG. 9 may reflect processing operations for generating the pulsatile and respiratory aspects of the PPG test signal. Pulsatile generation 904 may generally relate to generating a pulse signal based on the pulsatile profile, and may also include as an input the output of frequency modulation 902. Frequency modulation 902 may generate a frequency modulation component based on the respiratory profile. The pulse signal output from pulsatile generation 904 operations may be further modified based on amplitude modulation 906 and baseline modulation 908. Amplitude modulation 906 and baseline modulation 908 may be generated based on the respiratory profile. In some embodiments, the frequency modulated signal output from baseline modulation 908 may be the PPG test signal, while in other embodiments additional processing (e.g., based on the patient profile or artifact profile) may be performed to generate the PPG test signal.

Referring to the flow for frequency modulation 902, a signal generator 910 may generate a signal based on a respiration rate pattern RR(t) and frequency modulation phase $\theta_{FM}(t)$ that are based on the respiratory profile. Although signal generator 910 may generate any suitable signal type, in an exemplary embodiment the generated signal may be a sine wave having a phase and frequency based on the respiration rate pattern RR(t) and frequency modulation phase $\theta_{FM}(t)$. Although signal generator 910 (and other signal generators of FIGS. 9 and 10) may generate a signal in any suitable manner, in an exemplary embodiment signal generator 910 may be implemented using a combination of software and hardware. In an exemplary embodiment, the same respiration rate pattern RR(t) may also be input to signal generator 922 for generating the amplitude modulation signal and signal generator 926 for generating the baseline modulation signal. The respiration rate pattern RR(t) may include any suitable range of respiration rate, such as 3-60 breaths per minute. The respiration rate may be fixed or may vary in any suitable manner. In some embodiments, a user may select a fixed respiration rate, or may modify the respiration rate based on an input to test unit 302. In some embodiments, respiration rate patterns vary may be based on predetermined patterns associated with physiological activities such as sleep or exercise, physiological conditions such as apneic conditions, or treatments such as assisted breathing. In some embodiments, respiration rate patterns may vary randomly within a respiration rate range.

The frequency modulation phase $\theta_{FM}(t)$ may define a phase relationship compared to the phase of a pulsatile component of the signal $\theta_{PLETH1}(t)$, the phase of the amplitude modulation signal $\theta_{AM}(t)$, and the phase of the baseline modulation signal $\theta_{BM}(t)$. Each of these phase values may be selected and modified by a user of test unit 302, may be based on predetermined respiratory and pulsatile patterns (i.e., as determined by the respiratory and pulsatile profiles), or any combination thereof. In an exemplary embodiment the phase of a first pulsatile component phase $\theta_{PLETH1}(t)$ may be in phase with the baseline modulation signal phase $\theta_{BM}(t)$, the frequency modulation signal phase $\theta_{FM}(t)$ may have a 20° lag, and the amplitude modulation signal phase $\theta_{AM}(t)$ may be 180° out of phase.

Signal generator 910 may output the respiration modulation signal to amplifier 912. Amplifier 912 (as well as other amplifiers described in FIGS. 9 and 10) may be implemented in any suitable manner, including software, hardware, or a combination of hardware and software. Amplifier 912 may amplify the respiration modulation signal based on a gain value $G_{FM}(t)$ of the respiratory profile. The gain value $G_{FM}(t)$ may be selected and modified by a user of test unit 302, may be based on predetermined respiratory patterns, or any combination thereof. The resulting frequency modulation component may then be output to signal generator 914 and signal generator 918 of the pulsatile generation flow 904 to adjust the frequency and phase of the pulsatile signal based on frequency modulation component.

Signal generator 914 may generate a pulsatile signal component of the PPG test signal based on a pulse rate pattern PR(t) and the first pulsatile component phase $\theta_{PLETH1}(t)$ that are based on the pulsatile profile, as well as the frequency modulation component. Although signal generator 914 may generate any suitable signal type, in an exemplary embodiment the generated signal may be a sine wave having a phase and frequency based on the pulse rate pattern PR(t), the pulsatile component phase $\theta_{PLETH1}(t)$, and the frequency modulation component. The pulse rate pattern PR(t) may include any suitable range of pulse rate, such as 40-250 beats per minute. The pulse rate may be fixed or may vary in any suitable manner. In some embodiments, a user may select a fixed pulse rate, or may modify the pulse rate based on an input to test unit 302. In some embodiments, pulse rate patterns vary may be based on predetermined patterns associated with physiological activities such as sleep or exercise, physiological conditions such as known heart conditions, or treatment patterns such as heart pacing or medication. In some embodiments, the pulse rate patterns may vary randomly within a pulse rate range.

Signal generator 914 may output the pulsatile component to adder 920. The pulse rate pattern PR(t) may also be multiplied by multiplier 916 and provided to signal generator 918. Signal generator 918 may generate a harmonic component to be combined with the pulsatile component at adder 920. Although a single harmonic is described in herein, it will be understood that multiple harmonic components could be generated to be combined with the pulsatile component of the PPG test signal. In some embodiments, adding one or more harmonic signals to the fundamental pulsatile component may result in a PPG test signal that better matches the shape of an actual PPG signal. For example, a PPG signal may generally include a dichrotic notch that may be approximated as a second harmonic of the underlying pulse rate signal. Although additional components of the PPG test signal may be generated in any suitable manner, in an exemplary embodiment this signal morphology may be implemented by multiplying the pulse rate pattern by two at multiplier 916, and generating a second harmonic signal based on the output of multiplier 916, the frequency modulation component, and a second pulsatile component phase $\theta_{PLETH2}(t)$. The pulsatile component of the PPG test signal and the second harmonic component signals may then be combined at adder 920 to generate the pulse signal.

Referring to the flow for amplitude modulation 906, a signal generator 922 may generate a signal based on a respiration rate pattern RR(t) and amplitude modulation phase $\theta_{AM}(t)$ that are based on the respiratory profile. Although signal generator 922 may generate any suitable signal type, in an exemplary embodiment the generated signal may be a sine wave having a phase and frequency based on the respiration rate pattern RR(t) and amplitude modulation phase $\theta_{AM}(t)$. In an exemplary embodiment, the respiration rate pattern RR(t) of signal generator 922 may be the same respiration rate pattern RR(t) that is provided to signal generator 910 and signal generator 926.

Signal generator 922 may output the amplitude modulation signal to amplifier 924. Amplifier 924 may amplify the amplitude modulation signal based on a gain value $G_{AM}(t)$ that is based on the respiratory profile. The gain value $G_{AM}(t)$ may be selected and modified by a user of test unit 302, may be based on predetermined respiratory patterns, or any combination thereof. Although the gain may be set in any suitable manner, in an exemplary embodiment the gain may be defined based on a percentage modulation of the PPG test signal. For example, the percentage modulation may be based on the AC amplitude of the amplitude modulation signal divided by the AC amplitude of the fundamental frequency of the PPG test signal. The resulting amplitude modulation component may then be output to multiplier 930 to be combined with the pulse signal output from adder 920.

Although amplitude modulation may be implemented in any suitable manner, in an exemplary embodiment, the amplitude modulation may be implemented by multiplying the pulse signal from adder 920 with the amplitude modulation component output from amplifier 924. In an exemplary embodiment, the pulse signal may be modified by multiplying the pulse signal with the amplitude modulation component at multiplier 930. The amplitude of the resulting amplitude modulated pulse signal may vary based on respiration, such as is depicted in FIG. 4. The resulting amplitude modulated pulse signal may be provided to adder 932 to be combined with a baseline modulation component generated according to baseline modulation flow 908.

Referring to the flow for baseline modulation 908, signal generator 926 may generate a signal based on a respiration rate pattern RR(t) and amplitude modulation phase $\theta_{AM}(t)$ that are based on the respiratory profile. Although signal generator 926 may generate any suitable signal type, in an exemplary embodiment the generated signal may be a sine wave having a phase and frequency based on the respiration rate pattern RR(t) and baseline modulation phase $\theta_{BM}(t)$. In an exemplary embodiment, the respiration rate pattern RR(t) of signal generator 926 may be the same respiration rate pattern RR(t) that is provided to signal generator 910 and signal generator 922.

Signal generator 926 may output the baseline modulation signal to amplifier 928. Amplifier 928 may amplify the baseline modulation signal based on a gain value $G_{BM}(t)$ that is based on the respiratory profile. The gain value $G_{BM}(t)$ may be selected and modified by a user of test unit 302, may be based on predetermined respiratory patterns, or any combination thereof. Although the gain may be set in any suitable manner, in an exemplary embodiment the gain may be defined based on a percentage modulation of the PPG test signal. For example, the percentage modulation may be based on the AC amplitude of the baseline modulation signal divided by the AC amplitude of the fundamental frequency of the PPG test signal. The resulting baseline modulation component may then be output to adder 932 to be combined with the amplitude modulated pulse signal output from multiplier 930.

Although baseline modulation may be implemented in the PPG test signal in any suitable manner, in an exemplary embodiment, the baseline modulation may be implemented by adding the amplitude modulated pulse signal output from multiplier 930 to the baseline modulation component output from amplifier 928. In an exemplary embodiment, the amplitude modulated pulse signal and baseline modulation component may be combined at adder 932. The resulting respiration modulated signal may have a baseline that varies in accordance with the periodic changes in the baseline modulation component. In some embodiments the respiration modulated signal may be output without additional modulations due to additional profiles, and may be the PPG test signal. In the exemplary embodiment described herein, the respiration modulated signal may be further processed based on the patient profile and artifact profile. The flow may continue to FIG. 10 as indicated in FIG. 9.

The flow depicted in FIG. 10 may reflect processing operations for modifying the PPG test signal based on simulated patient characteristics, simulated artifacts, and other signal processing operations. For example, the flow depicted in FIG. 10 may include a patient characteristic flow 1002 and an artifact flow 1004.

Patient characteristic flow 1002 may relate to scaling or modifications of the simulated PPG signal based on patient characteristics. It will be understood that patient characteristic flow 1002 may not include all modulations of the PPG test signal due to patient characteristics, since other profiles (such as the pulsatile profile and respiratory profile) may also change in response to changes in patient characteristics.

Referring to the patient profile, the pulsatile blood flow indicated by a PPG signal may vary from patient to patient based on patient characteristics such as age, skin thickness, measurement location, patient cardiovascular health, or any other suitable patient characteristics. Although it will be understood that the patient characteristic flow may modify a PPG test signal in any suitable manner, in an exemplary embodiment the PPG test signal may be modified based on perfusion and transmissivity values of a patient profile.

In some embodiments, a perfusion signal P(t) and a transmissivity signal Tr(t) may be selected based on a patient profile. The signal values may be fixed, may vary over time based on a predetermined pattern, may vary randomly about a predetermined baseline value, may be based on known patient characteristics, or may be implemented in any other suitable manner. In an exemplary embodiment, a user of test unit 302 may select from among a set of patient characteristics such as age, sex, sensor location, body mass index, medications, known health conditions, any other suitable characteristic, or any combination thereof. Based on the selections, test unit 302 may generate a patient profile including a perfusion signal P(t) and a transmissivity signal Tr(t).

Although it will be understood that the perfusion signal P(t) and transmissivity signal Tr(t) may modify the PPG test signal in any suitable manner, in an exemplary embodiment the perfusion signal P(t) may modify the amplitude of the PPG signal while the transmissivity signal Tr(t) may modify the signal baseline. The respiration modulated signal and perfusion signal P(t) may be input to multiplier 1006, and the resulting signal may be input to adder 1008 along with transmissivity signal Tr(t). In some embodiments the resulting patient modulated signal may be output without additional modulations due to additional profiles, and may be the PPG test signal. In the exemplary embodiment described herein, the patient modulated signal may be further processed based on the artifact profile. The resulting patient modulated signal may be output from adder 1008 to artifact flow 1004.

Artifact flow 1004 may modify the patient modulated signal to simulate artifacts that cause non-physiological changes to a PPG signal. Although artifact flow may simulate any suitable artifacts, the artifacts may generally relate to motion artifacts and measurement artifacts that are part of an artifact profile. Motion artifacts may include artifact events due to irregular motion or artifacts due to regular patient motion. Motion artifacts may be selected from a set of predetermined artifact patterns, based on patient physiological characteristics and conditions (e.g., age, medications, or known health conditions), in any other suitable manner, or any combination thereof. Measurement artifacts may include artifact events due to the measurement equipment or process. For example, it may be desirable to simulate a particular type of sensor or sensor placement location. In some embodiments, a user of test unit 302 may input sensor characteristics or other measurement artifact parameters to generate the artifact profile. In some embodiments, a user of test unit 302 may select from among a set of known sensor types, sensor locations, or any other suitable measurement artifact parameters to generate the artifact profile.

Although it will be understood that artifacts may modify the patient modulated signal in any suitable manner, in an exemplary embodiment the artifacts may generally be categorized as multiplicative artifacts 1010 and additive artifacts 1012. Multiplicative artifacts may be combined with the patient modulated signal by multiplier 1014, while additive artifacts may be combined with the output of multiplier 1014 at adder 1016. The resulting PPG test signal may be output for additional processing (e.g., at truncating step 1018 and filtering step 1020).

At truncating step 1018, the values associated with the PPG test signal may be modified based on an analog to digital conversion rate and a sampling rate. A pulse oximeter may process a received PPG signal (e.g., at microprocessor 48) as a digital signal having a certain resolution and sampling rate. At truncating step 1018, the PPG test signal may be truncated to the nearest digital value based on a desired resolution. In addition, the time scale for samples of the PPG test signal may be selected based on a sampling rate. A user of the test unit 302 may select a desired resolution and sampling rate, may select from pulse oximeter types having known resolutions and sampling rates, or the resolution and sampling rate may be selected in any other suitable manner.

At filtering step 1020, the values of the samples of the PPG signal may undergo any other suitable filtering operations. For example, it may be known that a particular type of pulse oximeter performs filtering, smoothing, or interpolating operations before determining physiological parameters (e.g., pulse rate, oxygen saturation (SpO2), respiration rate, blood pressure), or that a sampled PPG signal is filtered in a particular manner before being output to another device for additional processing. For example, in some embodiments, a Bessel filter (e.g. at approximately 4 Hz) and a notch filter (e.g., at approximately 11 Hz) may be implemented at filtering step 1020.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method for generating an artificial photoplethysmograph (PPG) signal using a test unit, the method comprising:
    generating, using the test unit, a frequency modulation component, an amplitude modulation component, and a baseline modulation component based at least in part on a respiratory profile;
    generating, using the test unit, a pulse signal based at least in part on a pulsatile profile and the frequency modulation component;
    modifying, using the test unit, the pulse signal based at least in part on the amplitude modulation component and the baseline modulation component to generate a respiration modulated signal;
    generating, using the test unit, the artificial PPG signal based at least in part on the respiration modulated signal; and
    outputting, using the test unit, the artificial PPG signal to a physiological monitor.

2. The method of claim 1, wherein generating the pulse signal comprises:
    generating, a heart rate signal based at least in part on the pulsatile profile and the frequency modulation component;
    generating a dichrotic notch signal based at least in part on the pulsatile profile and the frequency modulation component; and
    combining the heart rate signal and the dichrotic notch signal.

3. The method of claim 1, wherein modifying the pulse signal comprises:
    multiplying, with a multiplier, the pulse signal and the amplitude modulation component; and
    combining, with an adder, the pulse signal and the baseline modulation component to generate the respiration modulated signal.

4. The method of claim 3, further comprising modifying, using the test unit, the respiration modulated signal based at least in part on a patient profile to generate a patient modulated signal.

5. The method of claim 4, further comprising modifying, using the test unit, the patient modulated signal based at least in part on an artifact profile to generate the artificial PPG signal.

6. The method of claim 5, wherein the pulsatile profile, respiratory profile, patient profile, and artifact profile are generated based at least in part on user inputs to a parameter selection interface.

7. The method of claim 4, wherein the patient profile comprises a perfusion signal and a transmissivity signal.

8. The method of claim 1, further comprising modifying, using the test unit, the respiration modulated signal based at least in part on an artifact profile to generate the artificial PPG signal.

9. The method of claim 1, wherein outputting the artificial PPG signal to the physiological monitor comprises simulating a sensor signal for the physiological monitor.

10. The method of claim 1, wherein the respiratory profile comprises:
    a respiration rate pattern;
    at least one of: a frequency modulation phase, an amplitude modulation phase, and a baseline modulation phase; and
    at least one of a frequency modulation gain, an amplitude modulation gain, and a baseline modulation gain.

11. A non-transitory computer-readable storage medium for providing an artificial photoplethysmograph (PPG) signal to a physiological monitor, the computer-readable medium comprising:
computer program instructions recorded thereon, wherein the computer program instructions, when executed by a test unit, cause the test unit to perform operations comprising:
generating a frequency modulation component, an amplitude modulation component, and a baseline modulation component based at least in part on a respiratory profile;
generating a pulse signal based at least in part on a pulsatile profile and the frequency modulation component;
modifying the pulse signal based at least in part on the amplitude modulation component and the baseline modulation component to generate a respiration modulated signal;
generating the artificial PPG signal based at least in part on the respiration modulated signal; and
outputting the artificial PPG signal to the physiological monitor.

12. The computer-readable medium of claim 11, wherein generating the pulse signal comprises:
generating a heart rate signal based at least in part on the pulsatile profile and the frequency modulation component;
generating a dichrotic notch signal based at least in part on the pulsatile profile and the frequency modulation component; and
combining the heart rate signal and the dichrotic notch signal.

13. The computer-readable medium of claim 11, wherein modifying the pulse signal comprises:
multiplying, with a multiplier, the pulse signal and the amplitude modulation component; and
combining, with an adder, the pulse signal and the baseline modulation component to generate the respiration modulated signal.

14. The computer-readable medium of claim 13, wherein the computer program instructions, when executed by the test unit, cause the test unit to further perform operations comprising:
modifying the respiration modulated signal based at least in part on a patient profile to generate a patient modulated signal.

15. The computer-readable medium of claim 14, wherein the computer program instructions, when executed by the test unit, cause the test unit to further perform operations comprising:
modifying the patient modulated signal based at least in part on an artifact profile to generate the artificial PPG signal.

16. The computer-readable medium of claim 15, wherein the pulsatile profile, respiratory profile, patient profile, and artifact profile are generated based at least in part on user inputs to a parameter selection interface.

17. A system for generating an artificial photoplethysmograph (PPG) signal, the system comprising:
a test unit comprising processing equipment configured to:
generate a frequency modulation component, an amplitude modulation component, and a baseline modulation component based at least in part on a respiratory profile;
generate a pulse signal based at least in part on a pulsatile profile and the frequency modulation component;
modify the pulse signal based at least in part on the amplitude modulation component and the baseline modulation component to generate the artificial PPG signal; and
output the artificial PPG signal to a physiological monitor.

18. The test unit of claim 17, wherein the processing equipment of the test unit is configured to:
generate a heart rate signal based at least in part on the pulsatile profile and the frequency modulation component;
generate a dichrotic notch signal based at least in part on the pulsatile profile and the frequency modulation component; and
combine the heart rate signal and the dichrotic notch signal.

19. The test unit of claim 17, wherein the processing equipment of the test unit is configured to:
multiply, with a multiplier, the pulse signal and the amplitude modulation component; and
combine, with an adder, the pulse signal and the baseline modulation component to generate the respiration modulated PPG signal.

20. The test unit of claim 19, wherein the processing equipment of the test unit is further configured to modify the respiration modulated signal based at least in part on a patient profile to generate a patient modulated signal.

21. The test unit of claim 20, wherein the processing equipment of the test unit is further configured to modify the patient modulated signal based at least in part on an artifact profile to generate the artificial PPG signal.

22. The test unit of claim 21, wherein the pulsatile profile, respiratory profile, patient profile, and artifact profile are generated based at least in part on user inputs to a parameter selection interface.

\* \* \* \* \*